United States Patent
Mooney, Jr.

(10) Patent No.: US 7,361,158 B1
(45) Date of Patent: Apr. 22, 2008

(54) CATHETER INCLUDING TEXTURED INTERFACE

(75) Inventor: Paul David Mooney, Jr., Tulsa, OK (US)

(73) Assignee: Medicinvent, LLC CA (US)

( * ) Notice: Subject to any disclaimer, the term of this patent is extended or adjusted under 35 U.S.C. 154(b) by 0 days.

(21) Appl. No.: 09/477,572

(22) Filed: Jan. 4, 2000

Related U.S. Application Data

(60) Provisional application No. 60/156,300, filed on Sep. 24, 1999.

(51) Int. Cl.
 *A61M 5/32* (2006.01)
(52) U.S. Cl. .................................... 604/174
(58) Field of Classification Search ............ 604/264, 604/290, 174, 175, 93.01, 265, 269, 523, 604/524–539, 284, 285, 286–288, 27–29; 600/585, 433, 434
 See application file for complete search history.

(56) References Cited

U.S. PATENT DOCUMENTS

| | | | | |
|---|---|---|---|---|
| 3,638,649 A | * | 2/1972 | Ersek | 604/8 |
| 3,700,380 A | * | 10/1972 | Kitrilakis | 623/3.29 |
| 4,046,144 A | * | 9/1977 | McFarlane | |
| 4,266,999 A | * | 5/1981 | Baier | 156/227 |
| 4,280,500 A | | 7/1981 | Ono | |
| 4,296,949 A | * | 10/1981 | Muetterties | |
| 4,362,156 A | * | 12/1982 | Feller, Jr. et al. | 604/165 |
| 4,413,985 A | * | 11/1983 | Wellner et al. | 604/9 |
| 4,676,782 A | * | 6/1987 | Yamamoto et al. | 604/175 |
| 4,940,458 A | | 7/1990 | Cohn | |
| 4,964,854 A | | 10/1990 | Luther | 606/73 |
| 5,098,435 A | * | 3/1992 | Stednitz et al. | 606/73 |
| 5,100,384 A | | 3/1992 | McBrien et al. | |
| 5,112,321 A | * | 5/1992 | Hiltebrandt | 604/264 |
| 5,248,298 A | * | 9/1993 | Bedi et al. | 604/51 |
| 5,258,003 A | * | 11/1993 | Ciaglia et al. | 606/185 |
| 5,267,975 A | | 12/1993 | Brodsky | |
| 5,273,545 A | * | 12/1993 | Hunt et al. | 604/167 |
| 5,295,994 A | | 3/1994 | Bonutti | |
| 5,308,338 A | * | 5/1994 | Helfrich | 604/175 |
| 5,380,304 A | | 1/1995 | Parker | |
| 5,403,292 A | * | 4/1995 | Ju | 604/282 |
| 5,409,469 A | * | 4/1995 | Schaerf | 604/282 |
| 5,431,655 A | * | 7/1995 | Melker et al. | 606/79 |

(Continued)

FOREIGN PATENT DOCUMENTS

FR 2773717 7/1999

*Primary Examiner*—Manuel Mendez
(74) *Attorney, Agent, or Firm*—Fellers, Snider, Blankenship, Bailey & Tippens, P.C.; Scott R. Zingerman

(57) ABSTRACT

A catheter including a body for insertion into a blood vessel of a medical patient. The body including an interface thereon which is the portion of the body that is inserted into and in contact with the skin or blood vessel of the patient. The interface includes texture on its exterior surface such that when the catheter body is inserted into the blood vessel, the texture secures the catheter body from migration at the point of entry of the catheter body into the patient. The texture is obtained by scoring or molding an irregular surface along the length of the interface. In the event that the catheter is configured for use with an introducer or cannula, portions of the introducer or cannula may also be textured in accordance with the invention.

14 Claims, 8 Drawing Sheets

U.S. PATENT DOCUMENTS

| | | | |
|---|---|---|---|
| 5,478,329 A * | 12/1995 | Ternamian | 604/274 |
| 5,496,289 A * | 3/1996 | Wenstrom, Jr. | 604/264 |
| 5,545,151 A * | 8/1996 | O'Connor et al. | 604/282 |
| 5,782,813 A | 7/1998 | Yoon | |
| 5,830,191 A * | 11/1998 | Hildwein et al. | 604/175 |
| 5,848,987 A * | 12/1998 | Baudino et al. | 604/500 |
| 5,957,928 A * | 9/1999 | Kirwan, Jr. | |
| 5,984,896 A | 11/1999 | Boyd | |
| 5,984,904 A * | 11/1999 | Steen et al. | |
| 6,033,382 A * | 3/2000 | Basta | 604/104 |
| 6,106,485 A * | 8/2000 | McMahon | 600/585 |
| 6,110,192 A * | 8/2000 | Ravenscroft et al. | 606/194 |
| 6,165,184 A * | 12/2000 | Verdura et al. | 606/148 |
| 7,008,412 B2 * | 3/2006 | Maginot | 604/523 |

* cited by examiner

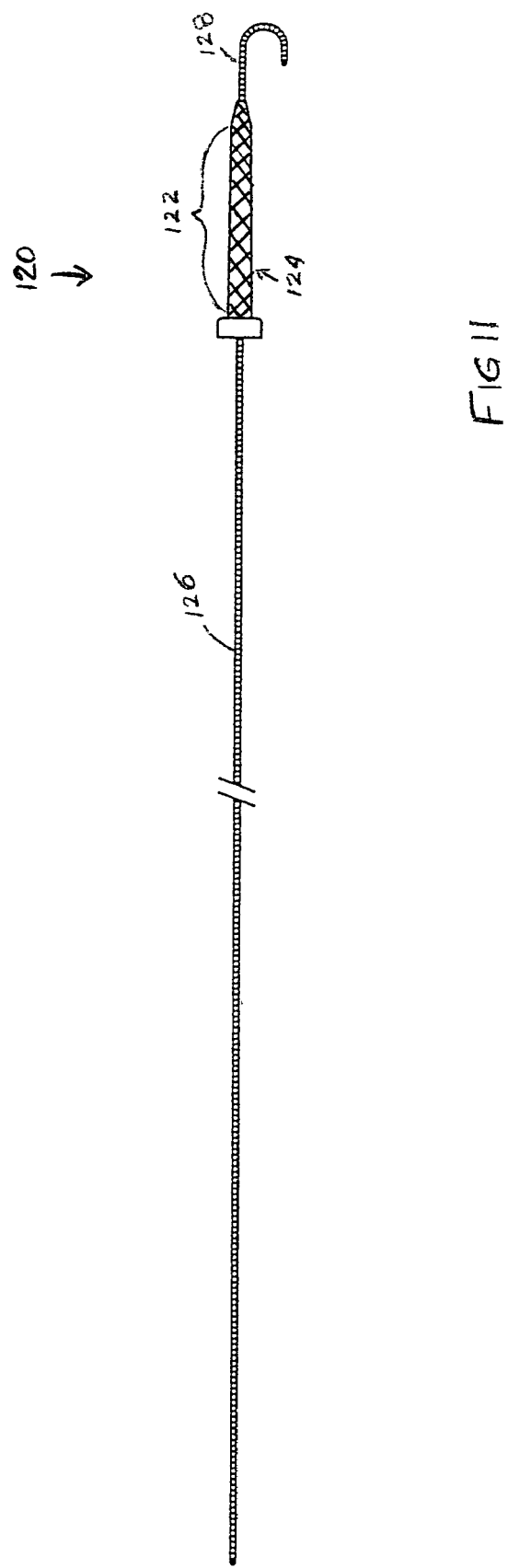

CATHETER INCLUDING TEXTURED INTERFACE

The present invention relates to the use of catheters for the introduction of fluids directly into the blood stream and claims benefit of prior filed copending Provisional Application No. 60/156,300, filed Sep. 24, 1999.

BACKGROUND OF THE INVENTION

Field of the Invention

Medical catheters are commonly used for the introduction of fluids into the bloodstream during medical procedures. Such catheters are available commercially in numerous embodiments designed specifically for such various medical procedures. These catheters are commonly inserted into the blood vessel of the patient through the use of an introducer or a needle and then held in place either by tape or by suturing the catheter to the blood vessel or surrounding tissue.

One problem commonly encountered in such procedures particularly where the catheter is inserted directly into the blood vessel and particularly during pediatric surgery is that the portion of the catheter which interfaces with the blood vessel is smooth, most generally comprised of plastic such that when an attempt is made to secure the catheter within the vessel, most commonly by tying a suture around the interfacing portion of the catheter, the pressure created by tightening of the suture causes the suture to eject or squirt from the blood vessel before it can be secured thereon. As a result, the possibility of contamination of the sterile catheter exists, not to mention the loss of valuable and expensive surgical time. A need therefore exists for a catheter which includes a textured interface so as to provide a frictional component to retain the catheter within the blood vessel while it is secured therein.

In addition to the use of catheters, intravenous stents (I.V.'s) are almost universally inserted into the dorsal vein of the hand when a person is admitted to a hospital or during the administration of a medical procedure. These intravenous stents, as well as many types of catheters, are designed to be maintained in the patient's body for a period of time which could exceed several days, weeks, or longer. In such situations the patient, if able, will be required to perform routine daily activities with the I.V. stent or catheter inserted in his or her body. Such routine activity and movement causes the portion of the I.V. or catheter which interfaces with the skin or blood vessel to move or migrate therein. A known concern is that such movement of the interface within the skin tissue or blood vessel may allow the introduction of infection causing organisms to enter the body or blood vessel. Such organisms may potentially result in a serious bodily infection. A need therefor exists for an I.V. stent and catheter which includes a textured interface to allow secure placement of the I.V. or catheter within the patient's skin tissue or blood vessel.

Central venous catheters have unique requirements to be maintained in a fixed position in the body to avoid migration and infection. Migration may produce serious vascular perforations, complications, and catheter infection produces sepsis both of which may be fatal complications.

Both complications will be reduced by improved fixation of the catheter and natural tissue attachment to the textured surfaces. Pediatric patients have especially difficult fixation problems due to larger catheter size to body size ratios and inability of the patient to cooperate in catheter long term care.

In addition, as the distance the catheter (or I.V.) body interface is positioned or secured from the situs of penetration into the patient's skin tissue/blood vessel increases, an increase in the resultant migration thereof is realized. As stated, the result of increased migration of the catheter (or I.V.) body interface is an increased risk of infection. A need, therefore, exists for a catheter or I.V. which is textured to restrain the catheter body interface within or adjacent the situs of penetration.

SUMMARY OF THE INVENTION

The present invention is a catheter including a body for insertion into a blood vessel of a medical patient. The body includes an interface thereon which is the portion of the body that is inserted into the blood vessel and is in contact therewith. A cannula may extend from the interface. The interface includes texture on its exterior surface such that when the body is inserted into the blood vessel, it can be secured therein without being ejected from the blood vessel during the process of securing the body within the blood vessel. As such, the textured interface provides sufficient frictional contact with the patient's skin or blood vessel so as to grip or retain the body therein while it is being tied or sutured in place. The texture thereby provides an increased surface area which is obtained by scoring or molding indentations within and along the length of the interface to provide such texture. Examples of suitable texture include diagonal cross-hatching or knurling, threading, concentric indentations cut along its length of either a fine depth and spacing or a coarse depth and spacing thereby providing ridges or concentric "donut" shapes along the length of the interface, or a plurality of cells or ridges positioned along the exterior surface of the interface. It is desirable that such texture provides increased surface area so as to achieve frictional contact between the interface and the blood vessel without causing damage to the blood vessel or surrounding tissue.

The texture of the present invention may also be used in alternate embodiment catheters which include a body having an interface thereon, a lumen for the introduction of liquids through the catheter, and wire guide obturator. In such an embodiment, the catheter is typically introduced through the skin and into the blood vessel such that the interface of the body is in direct contact with the skin tissue of the patient while the cannula pierces therethrough into and generally along the blood vessel. Catheters of this type are generally installed for periods of several days, weeks or longer for the long term introduction of fluids directly into the blood vessel. In such cases, the textured interface of the catheter body restricts movement of the catheter body within the skin tissue such that the tendency of the piercing wound to heal allows the skin cells (microplast) to grow in the texture thereby securing the catheter body from migration. In this way, the textured interface reduces and may eliminate the introduction of bacteria or fungi which have the potential of causing infection within the patient's body. A portion of the cannula may also be textured to further assist in securing the catheter from migration. It has been found that the catheter body should be fixed at the point of entry into the patient's body, as according to the present invention.

In addition, intravenous stents almost universally inserted into a patient's body during medical procedures may include a textured interface portion for the purpose of securing the stent within the patient's vein thereby also restricting the possibility of the introduction of infection causing organisms into the body or blood stream of the patient.

It is therefore an object of the present invention to include a catheter having a body including a portion which interfaces with the skin tissue or blood vessel of a patient during medical treatment wherein the interface is textured.

It is another object of the present invention to texture the interface of a catheter, and specifically an arterial or venous catheter to retain the catheter therein while it is secured in the patient's blood vessel.

It is still another object of the invention to provide an intravenous stent with a textured interface thereon.

A yet further object of the present invention is to provide a catheter or I.V. with a textured body interface thereby restraining this body interface within the situs of penetration into the patient's skin tissue/blood vessel.

BRIEF DESCRIPTION OF THE DRAWINGS

FIG. 11 is a view of a alternate embodiment catheter inducer which includes the textured interface of the present invention.

DETAILED DESCRIPTION OF THE PREFERRED EMBODIMENT

Figure 1:
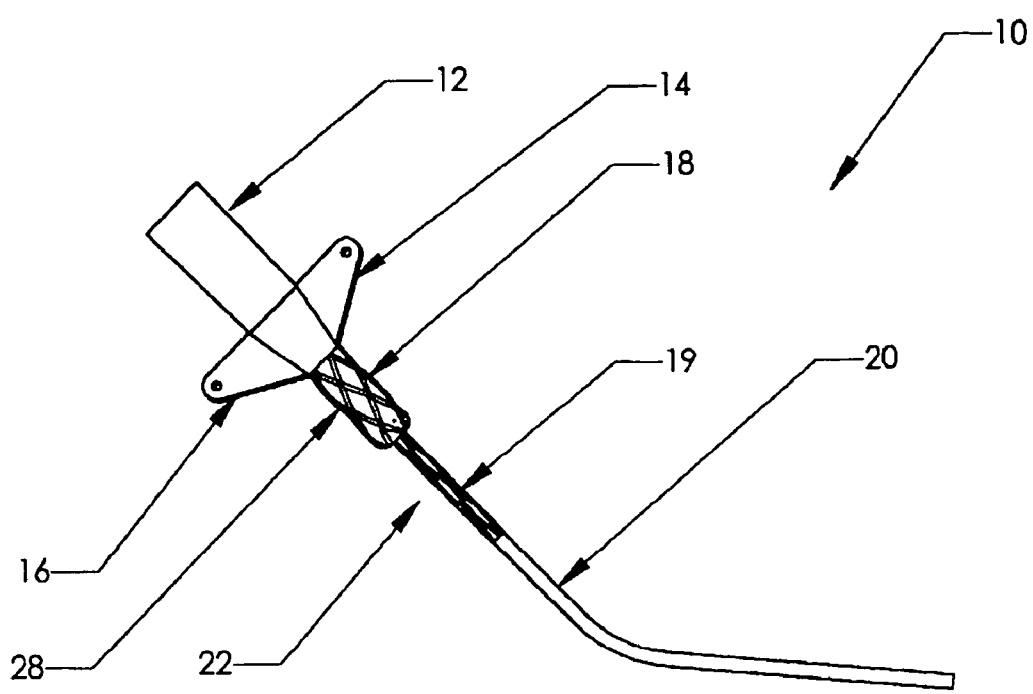
FIG. 1 depicts a central venous catheter which includes a textured interface of the present invention.
Figure 2:
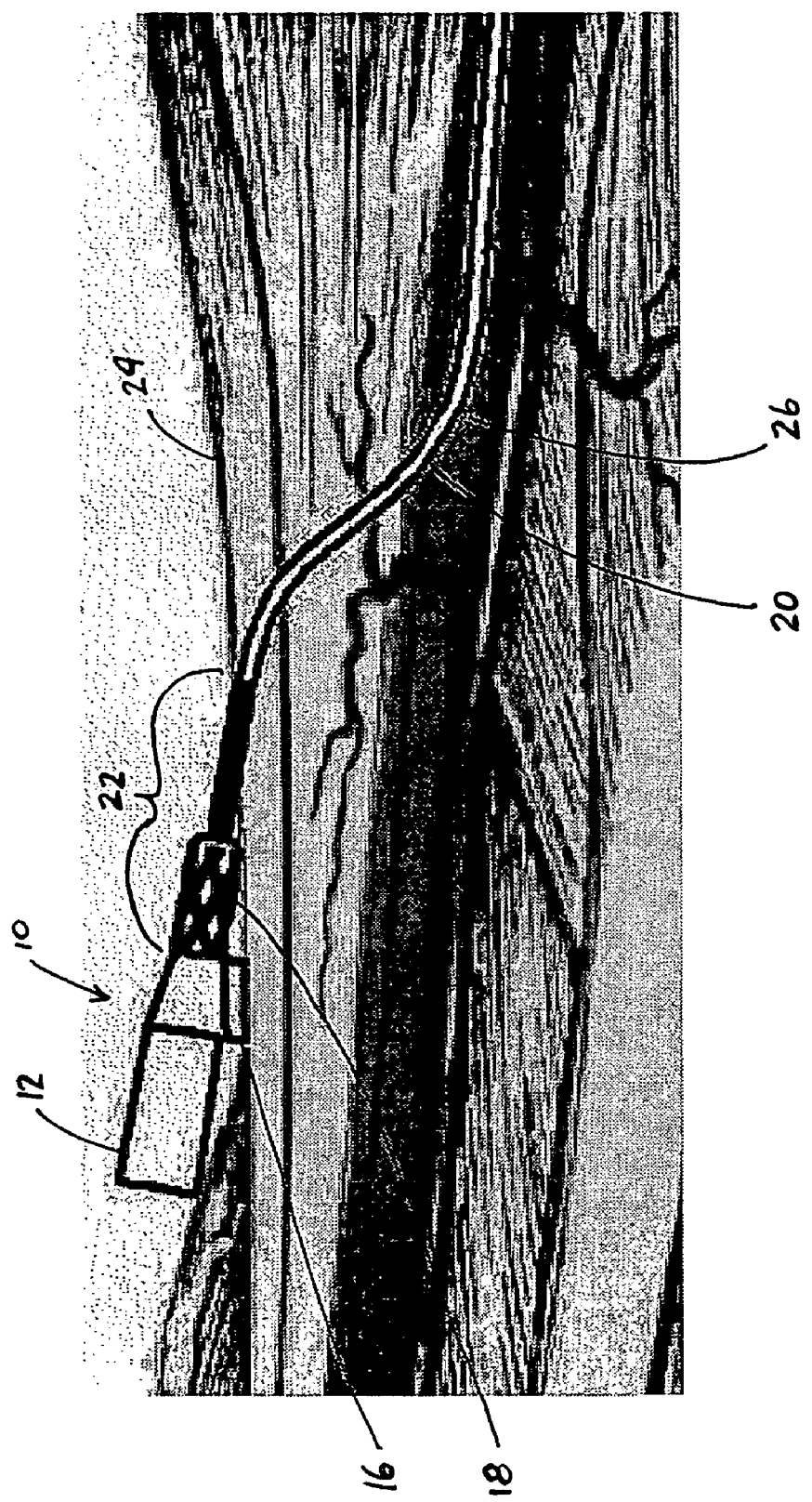
FIG. 2 is the central venous catheter of FIG. 1 wherein the knurled textured interface is depicted piercing and in contact with the skin of the patient.

FIG. 1 depicts a central venous catheter, and in particular, a peripherally inserted central venous catheter body 10 including lumen 12, wings 14 and 16, interface 18, and wire guide obturator 20 extending therefrom. Pursuant to the present invention, interface 18 includes a texture thereon such that when catheter 10 is inserted into a patient, the textured portion 22 of interface 18 is in contact with the patient's skin in order to keep catheter body 10 stationary therein. Referring more particularly to FIG. 2, where catheter body 10 is shown inserted through the skin 24 of a patient and into a vein 26. As such, cannula 20 extends from lumen 12 of catheter body 10 and into skin 24 and into vein 26. Interface 18 is the portion of catheter body 10 between cannula 20 and lumen 12. Interface 18 extends into the skin 24 of the patient. Texture 22 on interface 18 and or a portion of the first end of cannula 20 creates frictional contact between interface 18 (and cannula 20) of catheter body 10 and skin 24. Such frictional contact helps prevent catheter body 10 from moving or migrating within skin 24 or becoming dislodged therefrom.

Catheter body 10 is secured in place within the patient's body at the point of entry of interface 18 and cannula 20.

An additional important function of texture 22 is that the skin 24 (microplast) surrounding interface 18 will grow in an attempt to close or heal the hole (puncture) through which interface 18 and cannula 20 are inserted such that the cells will grow into engagement with the greater surface area of the interface caused by the texture in an attempt to close the puncture wound caused when the catheter was inserted. This interface between the cells of skin 24 and texture 22 of interface 18 will help deter interface 18 from moving in and out of skin 24 when the patient moves through activity. In this way, the possibility of infection causing germs from entering the puncture wound through skin 24 and the blood stream within vein 26 from the portion of interface 18 extending outside of skin 24 is greatly reduced. Such reduction in the possibility of the introduction of bacteria or fungus into the body is significant in the reduction of serious infection possibilities inherent in the use of the venous catheter. This infection risk is generally heightened by the typically weakened state of the patient's immune system as a result of the medical condition necessitating the use of the catheter.

The style of texture 22 in the preferred embodiment of FIG. 1 is a cross-hatching or knurling wherein lines are cut into the surface of interface 18 in a diagonal fashion along the annular, semi-cylindrical circumference of interface 18. The diagonal lines are cut such that they cross thereby forming discreet square or most commonly diagonal patterns 28. In that the diagonal lines are cut into the surface of interface 18, their crossing thereby defines discreet pattern 28 appearing raised above the circumference of interface 18. Each such discreet pattern 28 is separated from the next by the cross-hatched diagonal indentions. The particular geometric shape of individual pattern 28 is determined by the angle of the diagonal line cut in the surface of interface 18. For the purpose of exemplification, 500 microns is a suitable depth of texture 22, however, other depths are contemplated depending on the application.

Although texture 22 has been defined herein as being formed by cutting diagonal lines in the surface of interface 18, it is understood that other methods of manufacture are contemplated such as by injection molding the texture into the surface of interface 18 or such other manufacturing processes known in the art.

In addition, it is understood that individual configuration 28 could be defined by other types of indentions in interface 18 such as curved lines or perpendicular lines. Although the particular geometric design of FIG. 1 is preferred.

Figure 3:
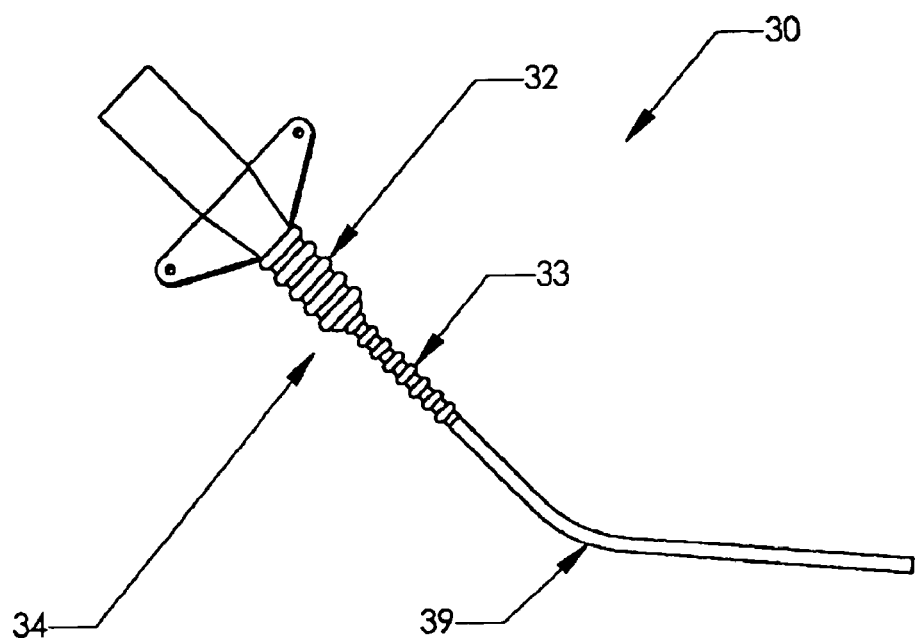
FIG. 3 is the central venous catheter of FIG. 1 configured with an alternate textured configuration including concentric rings cut in the length of the interface.

Referring next to FIG. 3, a first alternate embodiment texture is disclosed. Interface 32 of catheter 30 includes first alternate embodiment texture 34. First alternate texture 34 is defined by a series of concentric rings cut in the exterior circumference of interface 32. As with the preferred embodiment, the annular rings, as exemplified by ring 36 may be either cut in the surface of interface 32 or molded therein during the manufacture of catheter 30.

Annular rings 36 and 38 of texture 34 bound and define a discreet raised annular slice of interface 32. Each independent slice 37 may have equal diameters or may increase or reduce in diameter along the length of interface 32 as desired.

Catheter 30 may be substituted for catheter 10 in FIG. 2 such that wire guide obturator 39 pierces skin 24 and extends into vein 26 such that interface 32 engages skin 24 at the surface thereof and provides frictional contact therein. Texture 34 further provides the protection against infection as described above.

Figure 4:
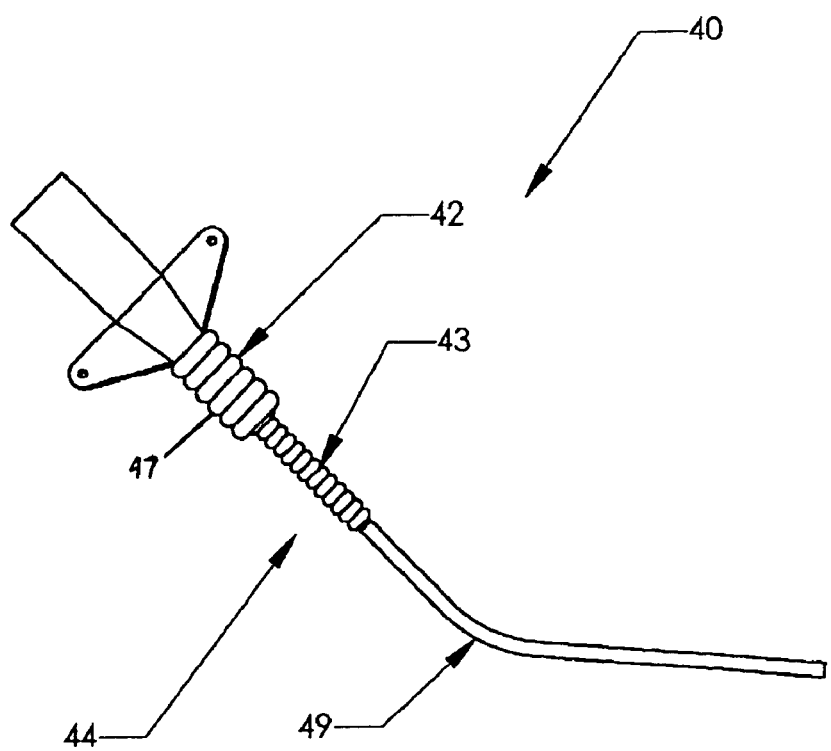
FIG. 4 is the central venous catheter of FIG. 1 configured with a second alternate textured configuration concentric rings having deeper channels than the first alternate textured configuration of FIG. 3.

FIG. 4 depicts a central venous catheter 40 including a second alternate embodiment texture 44 along interface 42. In this second alternate embodiment texture 42, the concentric rings, as exemplified by rings 46 and 48, are deeper in interface 42 defining a larger, more donut-shaped individual configuration as exemplified by configuration 47. Each individual "donut-shaped" texture configuration may be of equal size or increase or decrease in diameter along the length of interface 42 as desired for the required application or efficiency. Additionally, as stated above, texture 44 may be created in interface 42 at the time of its manufacture, typically by molding, or thereafter by a machine process.

Second alternate embodiment catheter 40 may be substituted for catheter 10 of FIG. 2 such that wire guide obturator 49 pierces skin 24 and enters vein 26 such that texture 44 pierces skin 24 in contact thereof.

Figure 5:
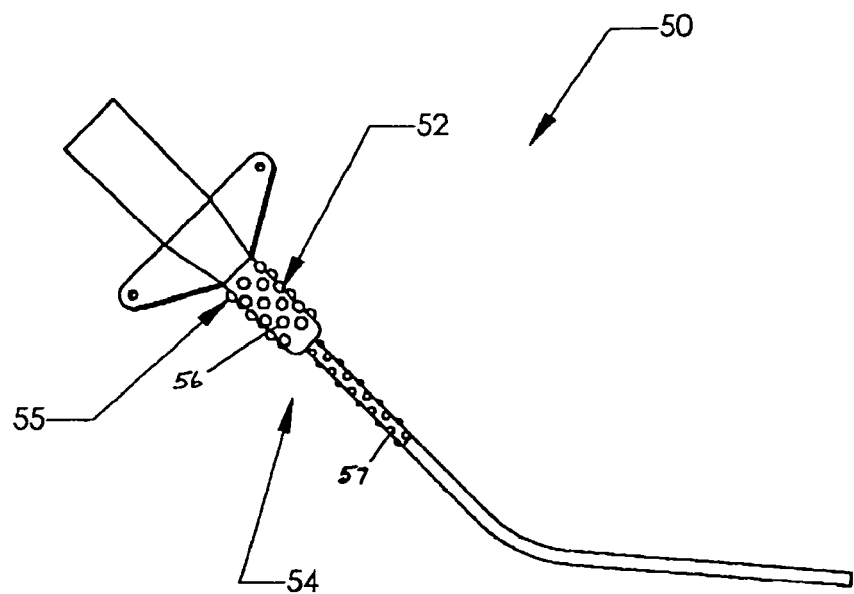
FIG. 5 is the central venous catheter of FIG. 1 configured with a third alternate textured configuration including integral raised cells or bumps on the interface.

Referring next to FIG. 5, wherein a central venous catheter 50 includes a third alternate embodiment texture 54 is disclose on interface 52. Third alternate texture embodiment texture 54 includes a series of cells or ridges 55-57 which extend above the cylindrical circumference of interface 52. Cells, or bumps, 55-57 may be formed in any known manner, however, it is believed that forming thereof during forming of interface 52 is the most efficient method. It is preferred that cells 55-57 be formed so as to provide a smooth texture and thereby rounded so as to minimize damage to the patient's tissue during use thereof. However, more pointed cells are contemplated in the invent that superior frictional capabilities of texture 54 are necessary.

Catheter 50 may be substituted for catheter 10 in FIG. 2 such that interface 52 extends into skin 24 and is in frictional contact therewith.

Figure 6:
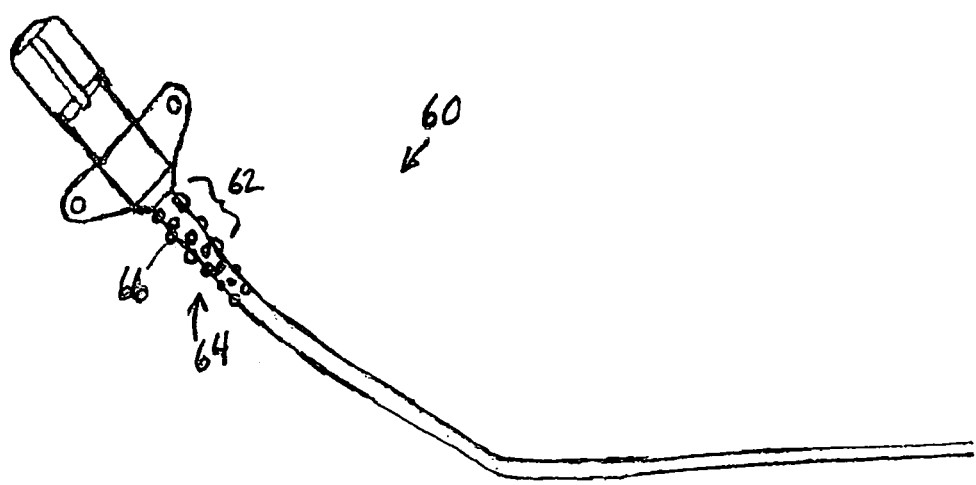
FIG. 6 is the central venous catheter of FIG. 1 configured with a fourth alternate texture configuration including cells or bumps which are smaller than the cells or bumps of the third textured configuration of FIG. 5.

Venous catheter 60 of FIG. 6 includes a plurality of smaller bumps, exemplified by bump 66 on interface 62. As can be seen, bump 66 is smaller than bump 55 of FIG. 5. As such, texture 64 of catheter 60 of FIG. 6 may be desirable for applications where less aggressive frictional contact between interface 62 and the surrounding patient's tissue is appropriate. The number of bumps such as bump 66 may be varied also as necessary. Bumps, such as bump 66, may be rounded or may have point thereon as desired for suitable applications.

Catheter 60 including texture 64 may be manufactured according to any suitable process. Catheter 60 may also be substituted for catheter 10 in FIG. 2 such that texture 64 of interface 62 is in contact with skin 24 upon insertion of catheter 60 through skin 24 into vein 26.

Figure 7:
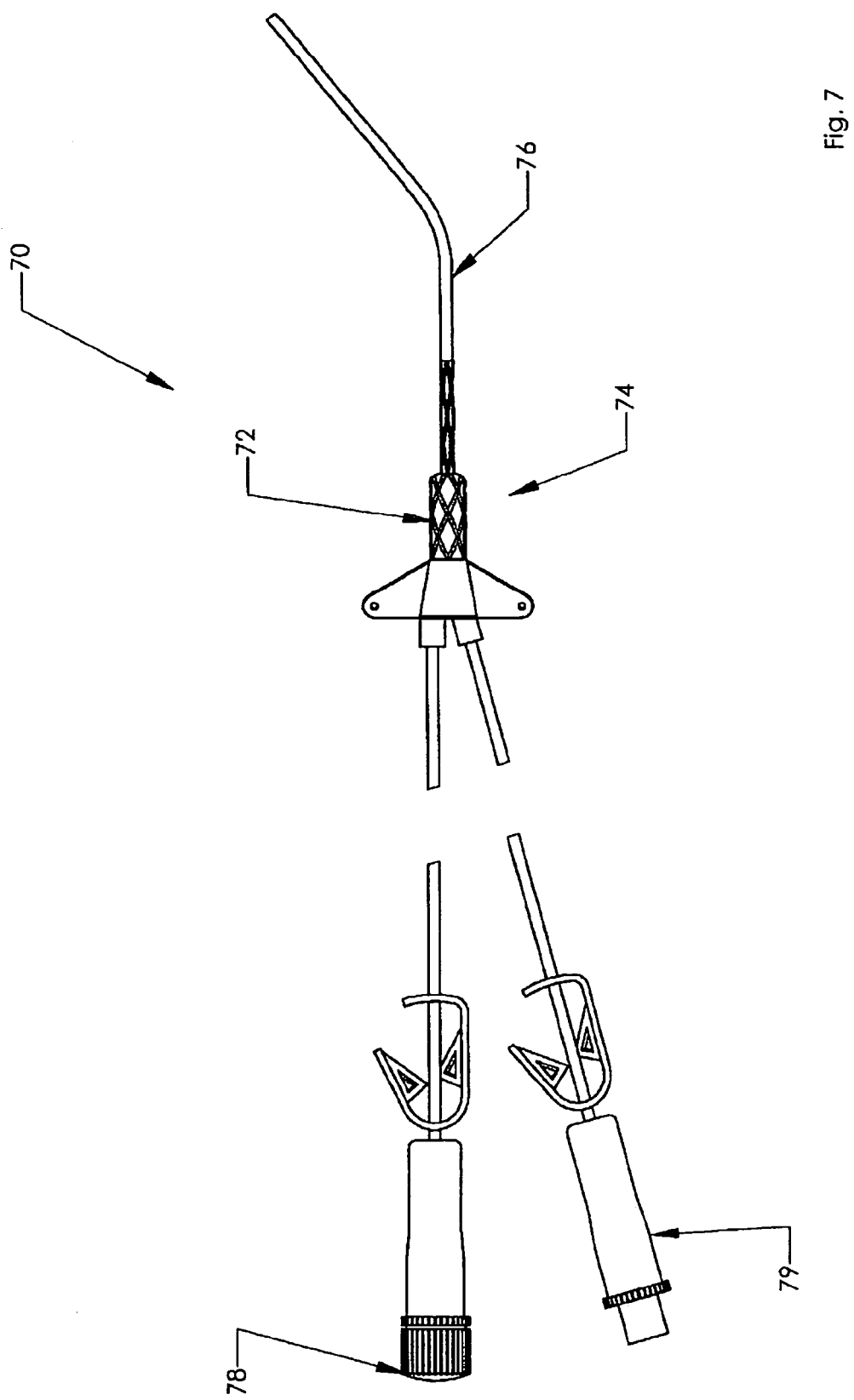
FIG. 7 depicts a plan view of a peripherally inserted central venous catheter (PICC) including textured interface.

FIG. 7 depicts a peripherally inserted central venous catheter (PICC) 70 wherein interface 72 includes texture 74 thereon. As can be seen, the portion of wire guide obturator 76 adjoining interface 72 may also be textured to allow greater frictional interaction with the surrounding tissue. PICC 70 is configured in a dual lumen configuration including a larger lumen 78 and a small lumen 79.

Figure 8:
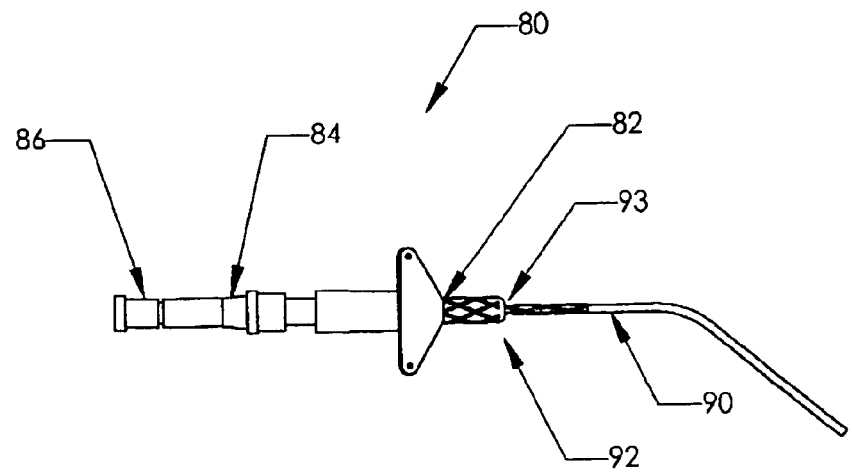
FIG. 8 is a plan view of an intravenous stent which includes the textured interface of the present invention.

FIG. 8 depicts an assembled intravenous stent assembly 80. Intravenous stent assembly 80 includes stent portion 82 and introducer/needle portion 84. Intravenous stent assemblies such as assembly 80 are commonly used to provide intravenous access to a medical patient.

Figure 9:
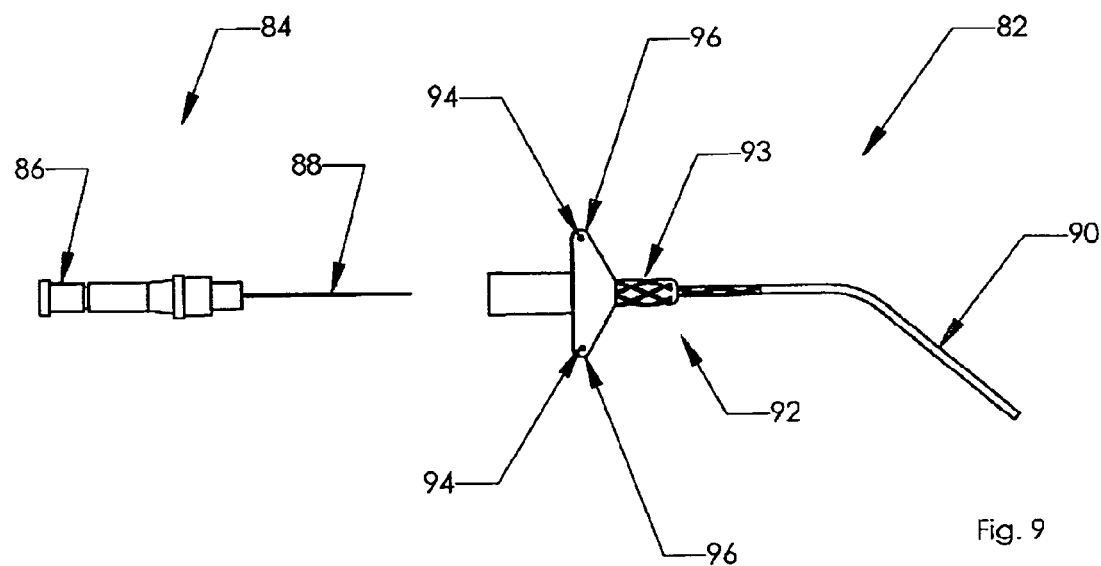
FIG. 9 is an exploded view of the intravenous catheter of FIG. 8 wherein the stent portion includes the textured interface of the present invention.

Taking FIG. 8 in combination with FIG. 9, intravenous stent assembly 80 includes stent portion 82, introducer/needle portion 84 and plug 86. In use, the assembled intravenous stent 80 (such as FIG. 8) is inserted into the patient's vein using needle 88. Intravenous stent assembly such as 80 are commonly inserted into a vein in the top of the patient's hand, wherein needle 88 and surrounding cannula 90 are inserted into the vein. Once inserted, intravenous fluids may be added by injection through plug 86 or by the removal of plug 86 and introduction through the hollow length of introducer 84.

Most commonly, however, once inserted, introducer/needle portion 84 is removed thereby leaving stent 82 within the hand of the patient such that cannula 90 and interface 92 extend into the vein. Once introduced, stent 82 is typically taped or sutured in place through holes 94 and wings 96. Introducer 92 of stent 82 includes texture 93 thereon. Texture 93 helps prevent stent 82 from being ejected by the vein. A portion of cannula 90 may also be textured, preferably adjacent introducer 92. Texture 93 also reduces movement of introducer 92 and thereby stent 82 within the vein. Thus, a secure intravenous stent provided.

Figure 10:
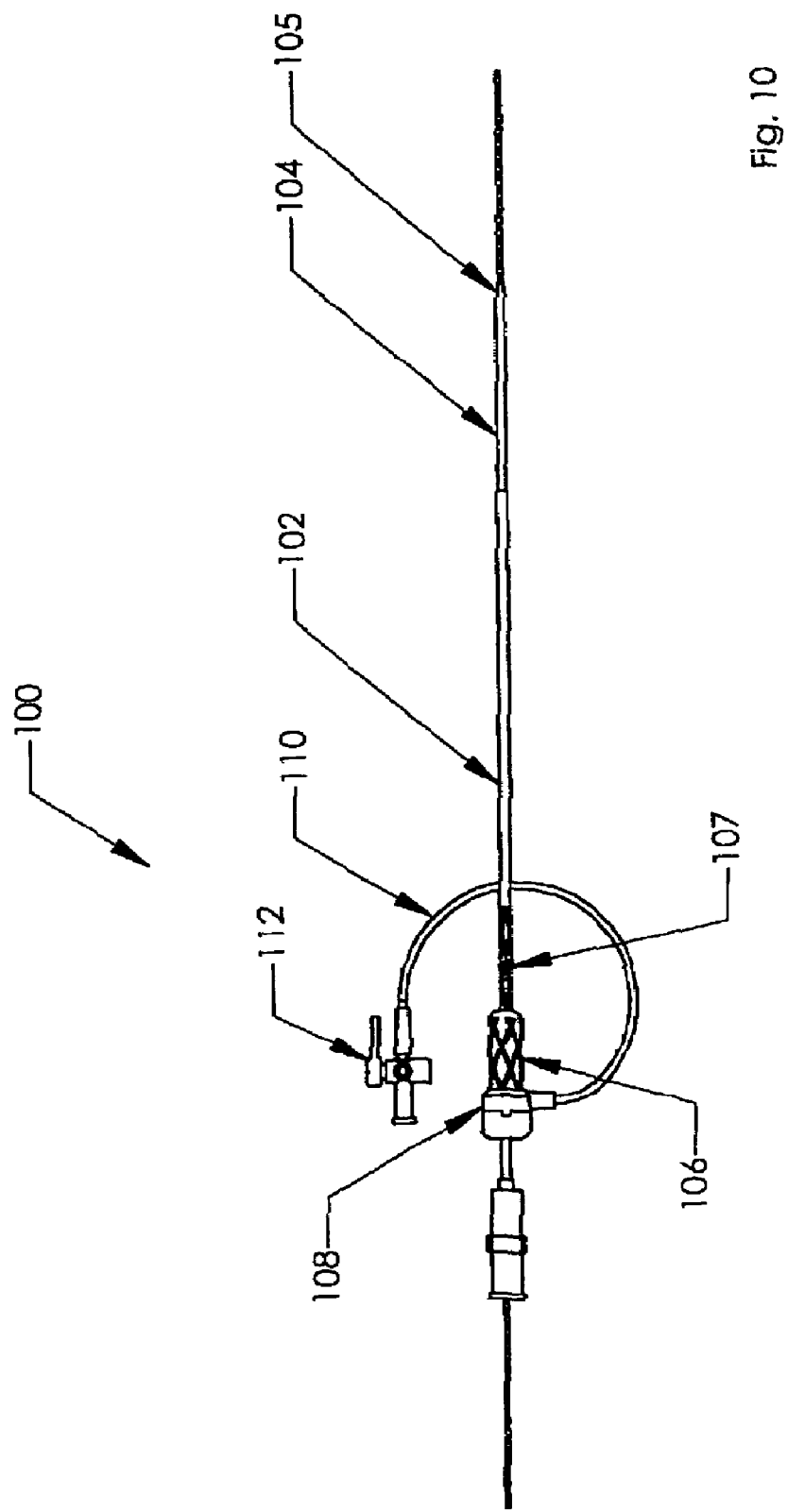
FIG. 10 is a plan view of a catheter inducer which includes the textured interface of the present invention.

FIG. 10 depicts a catheter introducer assembly 100. An introducer is also known in the art as a sheath or introducer sheath designed to allow controlled access to the body, minimize trauma to vein or artery and prevent excessive blood loss during a procedure. Introducers are available in many configurations to provide a sheath for introducing a catheter into the body.

Introducer 100 generally consists of two components, a sheath component 102 and a dilator component 104. Dilator 104 is longer than sheath 102 and is comprised of a smooth, stiff tube with a taper at its distal end 105. Dilator 104 fits within sheath 102. Taper 105 when inserted into the patient acts to dilate the tissue in the skin and vein to allow the sheath to pass thereafter. Once the introducer is inserted into a vein through the skin and positioned therein, introducer 100 allows a catheter to be inserted into the vein.

Sheath 102 of introducer 100 includes texture 106 and 107 thereon in order to provide frictional engagement with the skin and vein when sheath 102 is inserted. Texture 106 also restricts sheath 102 from movement within the vein in order to reduce the possibility of introduction of infection causing bacteria and fungi. A hub 108 includes a valve therein to prevent blood from leaking from the vein. A catheter is generally inserted through hub 108, sheath 102 and into the blood vessel to allow for the introduction of fluids therethrough. A side arm 110 terminating with a stop cock 112 is used to measure blood pressure and withdraw samples of blood for testing or otherwise.

FIG. 11 depicts introducer 120 for the insertion of guide wire 126 into a blood vessel to be followed by a catheter (such as PICC 70 of FIG. 7). Introducer body 120 is typically inserted directly into a severed vein such as in a angiogram procedure. Interface 122 of introducer body 120 includes texture 124 to provide frictional resistance while introducer body 120 is secured in the vein.

While the invention has been described with a certain degree of particularity, it is manifest that many changes may be made in the details of construction without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. An indwelling intravascular device for insertion into the bodily tissue and vessel of a medical patient thereby creating a puncture wound at the point of insertion and initiating the bodily process of healing the puncture wound, comprising:
   a body including an interface and a cannula;
   said cannula for extending into and terminating in the vessel;
   said body for at least partial insertion into the bodily tissue at the point of insertion;
   said interface having an outer dimension and being the portion of said body which remains in contact with said bodily tissue adjacent said point of insertion while the device remains inserted in the bodily tissue;
   said interface having an exterior surface including texture thereon wherein said texture does not substantially increase said outer dimension of said interface and said texture is constitutive of said exterior surface of said interface and wherein cells microplasts selected from the group consisting of fibroblasts, dermal, subdermal, inflammatory, and collagen grow into engagement with said texture during the bodily process of healing the puncture wound to form a barrier against the migration of foreign matter past said interface and to secure the catheter in place.

2. The indwelling intravascular device of claim 1 wherein a plurality of bumps are positioned on the exterior surface of said interface.

3. The indwelling intravascular device of claim 2 wherein the bumps are rounded.

4. The indwelling intravascular device of claim 2 wherein the bumps are pointed.

5. The indwelling intravascular device of claim 1 further including a wire guide obturator having a first end and a terminal end;
   said first end being secured to said interface;
   said first end including texture thereon.

6. The indwelling intravascular device of claim 1 wherein said texture is a static texture.

7. The indwelling intravascular device of claim 1 wherein the depth of the majority of said texture is between the range of 0.2 mm to 1.0 mm.

8. The indwelling intravascular device of claim 7 wherein the depth of the majority of said texture is between the range of 0.2 mm to 0.5 mm.

9. An intravenous stent for insertion into the bodily tissue of a medical patient at a point of insertion thereby creating a puncture wound at the point of insertion and initiating the bodily process of healing the puncture wound, comprising:
   a stent portion;
   said stent portion capable of receiving a needle therethrough;
   said stent portion including an introducer and a cannula through which said needle extends;
   said introducer including a proximal portion and a distal portion;
   a segment of said proximal portion for contact with the bodily tissue at the point of insertion and having an outer dimension;
   said introducer including texture on said segment of said proximal portion for contact with the bodily tissue at the point of insertion wherein said texture does not substantially increase said outer dimension of said introducer and said texture is constitutive of said exterior surface of said introducer and wherein cells microplasts selected from the group consisting of fibroblasts, dermal, subdermal, inflammatory, and collagen grow into engagement with said texture during the bodily process of healing the puncture wound to form a barrier against the migration of foreign matter past said interface and to secure the catheter in place.

10. The intravenous stent of claim 9 wherein a portion of said cannula includes texture thereon.

11. The intravenous stent of claim 10 wherein a portion of said cannula adjacent said introducer is textured.

12. The intravenous stent of claim 9 wherein said texture is knurling.

13. The intravenous stent of claim 9 wherein said texture includes a plurality of grooves cut into the exterior of said interface.

14. The intravenous stent of claim 9 wherein said texture includes a plurality of bumps positioned on its exterior surface.

* * * * *